United States Patent
Bernical (10) Patent No.: US 9,982,352 B2
(45) Date of Patent: May 29, 2018

(54) PRODUCTION OF DIHYDROGEN BY CONVERSION OF OVERHEAD GASES RESULTING FROM A SYNTHESIS

(71) Applicant: COMMISSARIAT A L'ENERGIE ATOMIQUE ET AUX ENERGIES ALTERNATIVES, Paris (FR)

(72) Inventor: Quentin Bernical, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 429 days.

(21) Appl. No.: 14/394,023

(22) PCT Filed: Mar. 7, 2013

(86) PCT No.: PCT/EP2013/054598
§ 371 (c)(1),
(2) Date: Oct. 10, 2014

(87) PCT Pub. No.: WO2013/152903
PCT Pub. Date: Oct. 17, 2013

(65) Prior Publication Data
US 2015/0152562 A1    Jun. 4, 2015

(30) Foreign Application Priority Data

Apr. 13, 2012 (FR) .................................. 12 53443

(51) Int. Cl.
   *C25B 1/02*             (2006.01)
   *C25B 15/08*           (2006.01)
   (Continued)

(52) U.S. Cl.
   CPC ................. *C25B 1/02* (2013.01); *C01B 3/32* (2013.01); *C01B 3/36* (2013.01); *C07C 1/04* (2013.01);
   (Continued)

(58) Field of Classification Search
CPC combination set(s) only.
See application file for complete search history.

(56) References Cited

U.S. PATENT DOCUMENTS 5,621,155 A    4/1997    Benham et al.
6,051,125 A    4/2000    Pham et al.
(Continued)

FOREIGN PATENT DOCUMENTS

FR        2 893 033 A1    5/2007
WO     00/17418 A1    3/2000
(Continued)

OTHER PUBLICATIONS

International Search Report (ISR) dated May 27, 2013 issued in corresponding application No. PCT/EP2013/054598; with English Translation; with Written Opinion of the International Searching Authority and English machine-translation.

*Primary Examiner* — Nicholas A Smith
(74) *Attorney, Agent, or Firm* — Westerman, Hattori, Daniels & Adrian, LLP (57) ABSTRACT

A chemical conversion process includes a synthesis step (10) that takes, as input, reactants that include at least dihydrogen and carbon monoxide and that gives, as output, a synthetic compound such as an engine fuel, water and overhead gases, a step of recovering all or some of the overhead gases resulting from the synthesis step and a step of producing dihydrogen, in particular electrochemically (14), by a conversion of the overhead gases recovered in the recovering step.

20 Claims, 4 Drawing Sheets

(51) Int. Cl.
    *C01B 3/32*    (2006.01)
    *C01B 3/36*    (2006.01)
    *C25B 1/04*    (2006.01)
    *C10K 3/04*    (2006.01)
    *C10G 2/00*    (2006.01)
    *C07C 1/04*    (2006.01)
    *C10J 3/00*    (2006.01)

(52) U.S. Cl.
    CPC ............... *C10G 2/32* (2013.01); *C10K 3/04* (2013.01); *C25B 1/04* (2013.01); *C25B 15/08* (2013.01); *C01B 2203/0205* (2013.01); *C01B 2203/025* (2013.01); *C01B 2203/062* (2013.01); *C10J 3/00* (2013.01); *C10J 2300/1618* (2013.01); *C10J 2300/1656* (2013.01); *C10J 2300/1684* (2013.01); *Y02E 60/366* (2013.01)

(56) References Cited

U.S. PATENT DOCUMENTS

| | | |
|---|---|---|
| 2003/0065042 A1 | 4/2003 | Shaw |
| 2003/0083390 A1 | 5/2003 | Shah et al. |
| 2007/0131909 A1 | 6/2007 | Rojey et al. |
| 2008/0023338 A1 | 1/2008 | Stoots et al. |
| 2008/0098654 A1 | 5/2008 | Cherry et al. |
| 2009/0235587 A1 | 9/2009 | Hawkes et al. |
| 2011/0041740 A1* | 2/2011 | Reilly ............ F23C 9/00 110/341 |
| 2015/0073188 A1* | 3/2015 | Floudas ............ C10G 35/00 585/332 |

FOREIGN PATENT DOCUMENTS

| | | |
|---|---|---|
| WO | 00/61707 A1 | 10/2000 |
| WO | 03/035590 A1 | 5/2003 |

\* cited by examiner

PRODUCTION OF DIHYDROGEN BY CONVERSION OF OVERHEAD GASES RESULTING FROM A SYNTHESIS

TECHNICAL FIELD OF THE INVENTION

One subject of the invention is a chemical conversion process comprising a synthesis step that takes, as input, reactants that include at least dihydrogen and carbon monoxide and that gives, as output, a synthetic compound such as an engine fuel, water and overhead gases.

One application that is particularly targeted relates to the chemical conversion of fuel products such as coal, oil, biomass or natural gas so as to form, at the end of the synthesis step, at least one synthetic compound consisting of a liquid engine fuel such as an alkane and/or an alkene.

PRIOR ART

The implementation of a synthesis step in a conversion process is a known and commonly used technique. It makes it possible to provide a desired synthetic compound from reactants such as carbon monoxide and dihydrogen. One general problem consists in obtaining a given and sufficient amount of dihydrogen upstream of the synthesis reactor.

Figure 1:
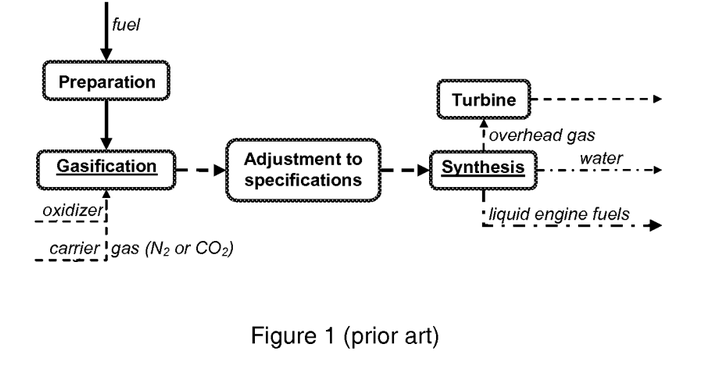
FIG. 1 is a view that illustrates the known principle of converting fuel products into liquid engine fuels.

This type of problem may be faced in a process for the chemical conversion of fuel products such as coal, oil, biomass or natural gas, so as to form, at the end of the synthesis step, water, overhead gases and above all at least one synthetic compound consisting of one or more liquid engine fuel(s) such as an alkane and/or an alkene. The conventional technique used for such a chemical conversion is illustrated in FIG. 1.

For solid fuels, the conversion process is based on two main steps: firstly a step of gasification of the solid fuel then, secondly, a step of synthesis of liquid engine fuels from gases obtained at the end of the gasification. Additional steps of reactant preparation and coproduct upgrading may complete the process. The reactants may be subjected to an adjustment to specifications between the gasification and the synthesis, whilst the overhead gases may be upgraded, for example by means of a turbine.

More specifically, the solid fuel is injected, after a preparation step suitable for the type of fuel and for the type of gasification, into a gasification reactor where the gasification step is carried out using a carrier gas (for example dinitrogen $N_2$ or carbon dioxide $CO_2$) and oxidised with the aid of an oxidizer such as dioxygen $O_2$. The role of the gasification is to generate a mixture of dihydrogen $H_2$ and carbon monoxide CO. These two compounds resulting from the gasification are the main reactants taken, as input, by the synthesis reactor where the synthesis step is carried out. The following equation presents the main balanced equations of the synthesis:

$$\begin{cases} n(CO + 2 + H_2) + H_2 \rightarrow C_nH_{2n+2} + n \cdot H_2O \\ n \cdot (CO + 2 \cdot H_2) \rightarrow C_nH_{2n} + n \cdot H_2O \end{cases}$$

In addition to the desired liquid engine fuels, the synthesis also produces water and a mixture of gases, subsequently referred to as "overhead gases". This mixture comprises:
- carbon monoxide and dihydrogen formed by the reactants not consumed during the synthesis;
- methane $CH_4$ and heavier gaseous compounds produced by the synthesis; and
- inert compounds, such as dinitrogen $N_2$.

Figure 2A:
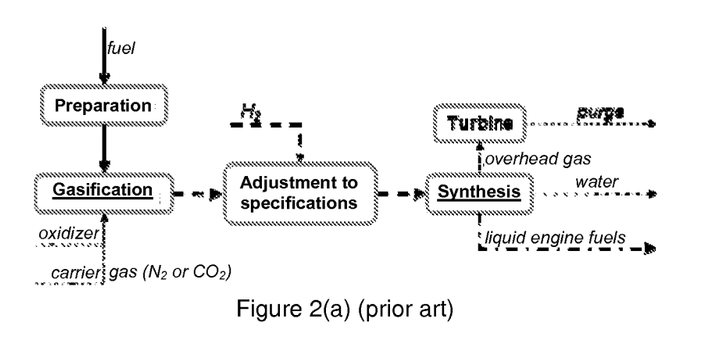

In the case of the production of conventional engine fuels such as diesel, the stoichiometric proportion between the dihydrogen and the carbon monoxide at the start of the synthesis must be slightly greater than two. However, the raw materials conventionally used (coal, biomass, etc.) do not make it possible to obtain such ratio, at the end of the gasification, between the carbon monoxide and the dihydrogen. Therefore, in order to maximize the use of the carbon contained in the fuels, it has been conceived, with reference to FIG. 2a, to add dihydrogen to the inlet of the synthesis reactor.

Figure 2B:
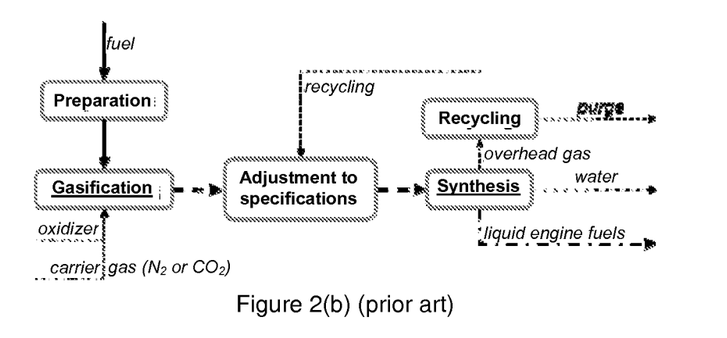
FIGS. 2b and 2c and 3 illustrate the known solution of recycling the overhead gases.
Figure 3:
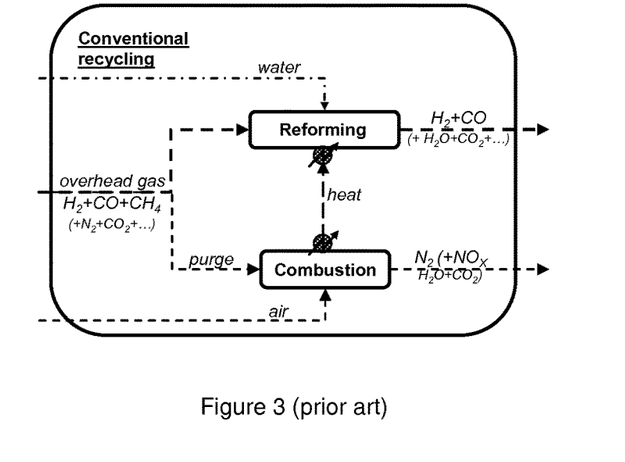

Moreover, it has been conceived, with reference to FIG. 2b, to recycle the overhead gases resulting from the synthesis, making it possible in particular to increase the productivity. The idea is not to produce dihydrogen but to recover the energy and material contained in the overhead gases at the outlet of the synthesis reactor. Such recycling is, for example, described in document US 2008/0098654 A1. Conventional recycling is shown schematically in FIG. 3. Only a fraction of the overhead gases is recycled, the remaining fraction of the overhead gases being purged in order to avoid the accumulation of inert compounds. Indeed, significant amounts of $N_2$ may in particular be injected in the gasification step if this gas is used as carrier gas for the fluidization, transport and injection of the (solid and previously ground) fuel. To a lesser extent, the fuel itself is composed of a small proportion of nitrogen, released during the gasification. The upgrading of this purge is the implementation of a step of combustion of the purged fraction of overhead gas (including an air supply) which provides energy in the form of heat needed for a reforming step (including a water supply) applied to the recycled fraction of overhead gas. If the amount is too large, the upgrading may be combustion in a boiler in order to recover heat, or in a gas turbine in order to produce electricity (it is the latter case which is represented in FIG. 1). These two solutions have a low efficiency (large entropic losses during the combustion) and lead to the production of pollutants in the form of nitrogen oxides $NO_x$.

Figure 2C:
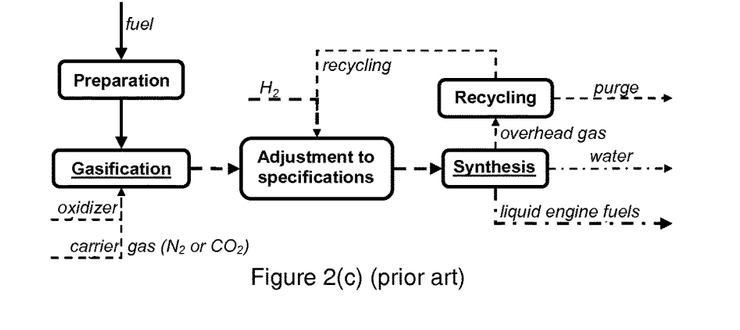

Although the combination (represented in FIG. 2c) of an addition of dihydrogen and of the recycling solution described previously has the advantages of an increase in the productivity (the ratio between the engine fuels and the base fuels being at least doubled in the case of biomass as raw material), of upgrading the energy (contained in the material) of the overhead gases, and of providing a technical solution for this upgrading, the fact remains that it involves the following drawbacks:
- it does not provide a technical solution for the production of dihydrogen,
- it has a low (entropic and energy) efficiency,
- the upgrading of the energy (contained in the material) of the overhead gases is limited in the cases where the purge is too large,
- the polluting production of $NO_x$ during the combustion of the amount purged,
- and a dilution of the carbon dioxide during the combustion of the amount purged.

Figure 4:
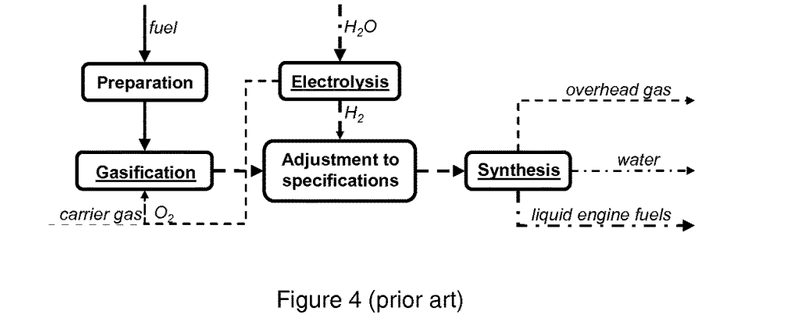

A second solution, with reference to FIG. 4 and for example described in document US 2008/0023338 A1, makes provision for a production of dihydrogen using a high-temperature steam electrolysis (known under the acronym HTSE) by dissociating water based on the following equation:

$$H_2O \rightarrow H_2 + \frac{1}{2} \cdot O_2$$

Figure 5:
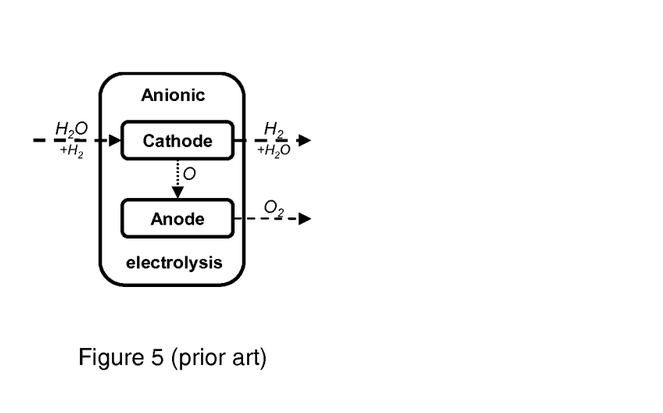

The associated electrolyzers use solid oxides as electrolyte. This solution, referred to as anionic, separates oxygen from the reactants (here, water) as is represented by FIG. 5. It also makes it possible to consume the heat generated at various points of the conversion process in order to vaporize the water. The electrolysis of water furthermore makes it possible to produce pure dioxygen $O_2$ used during the gasification step. The use of electrochemical solutions for production of dihydrogen and dioxygen is proposed in document US 2008/0098654 A1 which uses the recycling solution, but is also described for example in document US 2009/0235587 A1 which presents numerous options for use of the heat for HTSE but does not provide a solution for upgrading the overhead gases.

Although the electrolysis solution described above has the advantages of providing a technical solution for the production of dihydrogen and a simultaneous production of dioxygen, of good (energy and entropic) efficiency, the fact remains that it involves the following drawbacks in the case where it is combined with a recycling step:
- it has a low (entropic and energy) efficiency due to the recycling,
- upgrading of the energy (contained in the material) of the overhead gases is limited in the cases where the purge is too large,
- the polluting production of $NO_x$ during the combustion of the amount purged,
- and a dilution of the carbon dioxide during the combustion of the amount purged.

The solutions for recycling overhead gases described in documents US 2003/065042 A1, WO 035590 A1 and U.S. Pat. No. 5,621,155 A have the same drawbacks.

SUBJECT OF THE INVENTION

The object of the present invention is to propose a chemical conversion solution that overcomes the drawbacks listed above.

In particular, one subject of the invention is to improve the efficiency of the solution.

Another subject of the invention is to improve the upgrading of the energy (contained in the material) of the overhead gases.

Another subject of the invention is to reduce or even eliminate the pollutions induced.

Another subject of the invention is to limit or even eliminate the dilution of the carbon dioxide induced by the use of the solution.

A first aspect of the invention relates to a chemical conversion process comprising a synthesis step that takes, as input, reactants, that include at least dihydrogen and carbon monoxide, and that gives, as output, a synthetic compound such as an engine fuel, water and overhead gases. It comprises:
- a step of recovering all or some of the overhead gases resulting from the synthesis step; and
- a step of producing dihydrogen, electrochemically, by a conversion of the overhead gases recovered in the recovering step.

Preferably, it is a step of electrochemical production of dihydrogen by a conversion of the overhead gases recovered in the recovering step, electrochemically and in a manner that creates dihydrogen.

The process may comprise a step of transferring the dihydrogen formed in the dihydrogen production step to an inlet of a synthesis reactor that carries out the synthesis step.

A step of cracking the overhead gases resulting from the synthesis step may advantageously be carried out.

The dihydrogen production step may comprise a step of assisted electrolysis, on the anode side of an electrochemical device, by the overhead gases recovered in the recovering step.

The process may comprise a step of receiving all or some of the water resulting from the synthesis step, the assisted electrolysis step using water recovered in the receiving step.

The electrolysis carried out in the assisted electrolysis step may be of anionic type and carries out:
- a reduction reaction from water, on the cathode side of the electrochemical device, producing on the one hand dihydrogen that constitutes the dihydrogen formed in the production step, and on the other hand oxygen,
- a combustion reaction on the anode side, between the oxygen resulting from the reduction reaction and the overhead gases recovered in the recovering step, in order to produce water and carbon dioxide.

The cracking step may then be applied to the gases recovered in the recovering step using steam formed from the water recovered in the receiving step and/or a reused fraction of the total amount of water resulting from the assisted electrolysis step.

A step of collecting carbon dioxide produced during the combustion reaction at the anode may also be carried out.

The process may also advantageously comprise a step of heat exchange between fluids chosen from the following list: overhead gases recovered during the recovering step, dihydrogen and/or water and/or carbon dioxide and/or dinitrogen resulting from the assisted electrolysis step, gases resulting from the cracking step, water recovered during the receiving step and carbon dioxide recovered during the collection step.

Alternatively, the electrolysis carried out in the assisted electrolysis step may be of protonic type and carries out:
- an oxidation reaction on the anode side, from water and gases recovered during the recovering step, producing carbon dioxide,
- a reduction reaction on the cathode side of the electrochemical device, in order to create dihydrogen that constitutes the dihydrogen formed in the production step.

Fuel products such as coal, oil, biomass or natural gas are especially converted so as to form, at the end of the synthesis step, at least one synthetic compound consisting of a liquid engine fuel such as an alkane and/or an alkene.

The process may comprise a gasification step, in a gasification reactor, that takes, as input, at least said fuel products and that gives, as output, reactants that include at least one portion of the dihydrogen and of the carbon monoxide used during the synthesis step.

The process may also comprise a step of transferring the carbon dioxide recovered during the carbon dioxide collection step to an inlet of the gasification reactor in order to form a carrier gas during the gasification step.

A step of recycling the fraction of overhead gas resulting from the synthesis step and not recovered during the overhead gas recovering step may be carried out, and also a step of electrolysis of water, in particular of high-temperature steam electrolysis type, using the fraction of water resulting from the synthesis step and not recovered during the water receiving step.

The process may comprise a step of transferring dihydrogen produced during the water electrolysis step to an inlet of the synthesis reactor that carries out the synthesis step and/or a step of transferring dioxygen produced during the water electrolysis step to an inlet of the gasification reactor that carries out the gasification step in order to form an oxidizing compound during the gasification step.

A second aspect of the invention relates to a chemical conversion plant, especially for conversion of fuels such as coal, oil, biomass or natural gas, into at least one synthetic compound, especially a liquid engine fuel such as an alkane and/or an alkene, this plant comprising the equipment and/or software components that carry out the conversion process described above.

Finally, a third aspect of the invention relates to a computer program comprising a computer program code means suitable for the production of the steps of the process, when the program is executed by a computer.

BRIEF DESCRIPTION OF THE DRAWINGS

Other advantages and features will emerge more clearly from the following description of particular embodiments of the invention given by way of nonlimiting examples and represented in the appended drawings, in which:

FIGS. 2a and 2c, 4 and 5 illustrate the known solution of supply of dihydrogen obtained by electrolysis of water.

DESCRIPTION OF PREFERRED EMBODIMENTS OF THE INVENTION

The principles of the invention will be set out below in relation to FIGS. 6 to 9.

The invention relates, generally, to a chemical conversion process comprising a synthesis step 10 that takes, as input, reactants that include at least dihydrogen $H_2$ and carbon monoxide CO and that gives, as output, mainly a synthetic compound such as an engine fuel, but also water and overhead gases.

The invention especially relates to the synthesis of an engine fuel of liquid nature. However, the invention may be extended to any process for which an addition of dihydrogen is beneficial and that has a co-production of poorly upgraded energy compounds that can be likened to the overhead gases described here, with adjustments on a case-by-case basis. For example, in order to extend it to gaseous fuels, an additional step of separation of the gases at the outlet of the synthesis 10 into undesired compounds and desired gaseous fuels is necessary.

The overhead gases essentially comprise:
  carbon monoxide and dihydrogen formed by the reactants not consumed during the synthesis 10;
  methane $CH_4$ and heavier gaseous compounds produced by the synthesis;
  inert compounds, such as dinitrogen $N_2$.

In particular, it is one such conversion process in which fuel products such as coal, oil, biomass or natural gas are converted so as to form, at the end of the synthesis step 10, at least one synthetic compound consisting of a liquid engine fuel such as an alkane and/or an alkene. The synthesis step 10 is carried out in a synthesis reactor. Biomass, which is a compound mainly formed of carbon, hydrogen and oxygen (up to 50% by weight of oxygen), is a fuel in itself.

The chemical conversion process also comprises a step 11 of gasification of the fuel products, carried out in a gasification reactor and intended to form the reactants provided at the inlet of the synthesis step 10. More specifically, the solid fuel products are injected with the aid of a carrier gas (for example dinitrogen $N_2$ or carbon dioxide $CO_2$), after a preparation step 12 adjusted to the type of fuels and the type of gasification 11, in the gasification reactor and oxidized by an oxidizer such as dioxygen $O_2$. For gaseous fuel products, the use of the carrier gas is superfluous, moreover, the step 11 of oxidation by an oxidizer such as dioxygen $O_2$ or water $H_2O$ could also be referred to as reforming. In other words, the gasification step 11 takes, as input, at least said fuel products and gives, as output, reactants that include at least one portion of the dihydrogen and of the carbon monoxide used during the synthesis step 10. Indeed, additional dihydrogen may also be added in a manner as described below. The role of the gasification 11 is to generate a mixture of dihydrogen $H_2$ and carbon monoxide CO provided to the synthesis reactor. The reactants may, beforehand, undergo a step 13 of adjustment to the specifications between the gasification 11 and synthesis 10.

According to one important feature, the conversion process comprises a step of recovering all or some of the overhead gases resulting from the synthesis step 10 and a step of producing dihydrogen, electrochemically, at a hydrogen pump 14, the operation of which will be described in detail further on, by a conversion of the overhead gases recovered in the recovering step.

Optionally, but very advantageously, the conversion process may also include a known step 15 of water electrolysis, especially of high-temperature steam electrolysis "HTSE" type, and/or a step 16 of recycling the optional fraction of overhead gas resulting from the synthesis step 10 and not recovered during the overhead gas recovering step. The principles of the conventional electrolysis step 15 have been described above with reference to FIGS. 4 and 5 and are incorporated here. The principles of the recycling step 16 have also been described above with reference to FIGS. 2 and 3 and are incorporated here too. In the event of such a recycling step 16 being carried out, the overhead gases recovered in the recovering step correspondent concretely to the purged fraction of overhead gas used during the recycling step 16.

As indicated above, provision may be made for the dihydrogen formed in the dihydrogen production step by the hydrogen pump 14 to be transferred 29 to an inlet of the synthesis reactor in order to be added to the dihydrogen already produced by the gasification step 11, so as to guarantee that the stoichiometric proportion between the dihydrogen and the carbon monoxide at the inlet of the synthesis reactor is slightly greater than two. The amount of dihydrogen optionally resulting from the water electrolysis step 15 and/or recycling step 16 may also be added upstream of the synthesis step 10.

Figure 7:
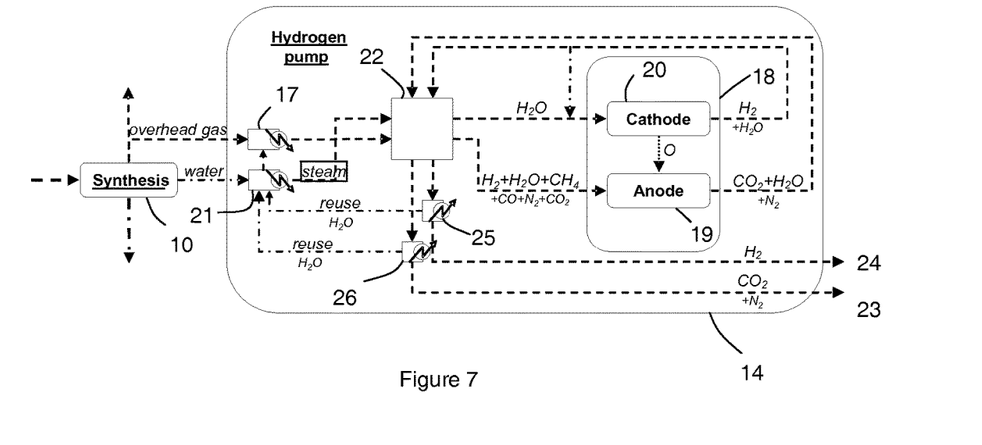
FIG. 7 represents the operating principle of a hydrogen pump used in FIG. 6, in its anionic operating version.

The operation of the hydrogen pump 14 that carries out the step of electrochemical production of dihydrogen by conversion of the overhead gas fraction recovered in the recovering step is now described in relation to FIG. 7. The hydrogen pump 14 receives, at the inlet, the fraction of overhead gas recovered in the recovering step with a view to converting the latter electrochemically in a manner that makes it possible to create dihydrogen.

Mainly, the step of electrochemical production of dihydrogen by the hydrogen pump 14 comprises an assisted electrolysis step 18, on the anode 19 side of an electrochemical device, using the overhead gases recovered in the recovering step. Such an electrochemical device, in other applications, is known for example from document WO 2000/017418, the teachings of which are incorporated here. It may be an assisted electrolysis of anionic type (FIG. 8) as described here or of protonic type (FIG. 9), the respective principles of which will be described in detail further on. The electrochemical device that carries out the assisted electrolysis 18 at the anode 19 using the overhead gases recovered also comprises a cathode 20. Such an assisted electrolysis consists in using the overhead gases at the anode 19 in a manner that makes possible to promote (by lowering the potential difference) the electrolysis of the water sent to the cathode 20 (or to the anode 19 in the protonic case), compared to a conventional electrolysis (FIG. 5) in which no overhead gas would be sent to the anode 19.

As illustrated in FIG. 7, a step of receiving all or some of the water resulting from the synthesis step 10 may be carried out. This water that is collected is taken, as input, by the hydrogen pump 14 so that the assisted electrolysis step 18 can use the water recovered in the receiving step. Beforehand, the received water may undergo a vaporization step 21 (also with a view to an optional cracking step 17 of the overhead gases recovered, described in detail further on).

Figure 8:
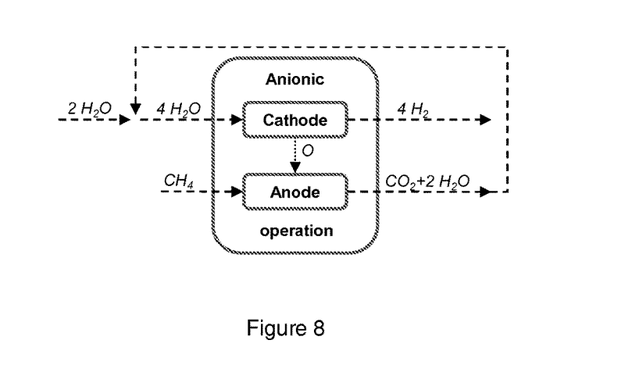
FIGS. 8 and 9 illustrate the respectively anionic and protonic operating principle of the assisted electrolysis carried out in FIG. 7.

In the case of anionic operation with reference to FIGS. 7 and 8, the electrolysis carried out in the assisted electrolysis step 18 carries out:
- a reduction reaction from water, on the cathode 20 side, producing on the one hand dihydrogen that constitutes the dihydrogen formed in the electrochemical production step, and on the other hand oxygen in a form other than dioxygen,
- a combustion reaction on the anode 19 side, between the oxygen resulting from the reduction reaction above and the overhead gases recovered in the recovering step, in order to produce water and carbon dioxide.

At the outlet of the hydrogen pump 14, the dihydrogen produced during the assisted electrolysis step 18 is captured, which is represented by reference 24. The amount of dihydrogen captured 24 is equal to that produced but may however be less than that leaving the cathode 20, since a portion may be reinjected at the cathode 20.

The carbon dioxide produced during the combustion reaction at the anode 19 may advantageously be collected during a collection step 23. This amount of carbon dioxide has the advantage of being diluted very little or not at all.

The electrochemical device which carries out the assisted electrolysis step 18 is therefore overall a combination of an electrolyzer for creating dihydrogen and dioxygen, and a fuel cell (owing to the presence of overhead gases at the anode 19) that carries out the combustion of the dioxygen at the anode 19. The combined use of an electrolyzer and of a fuel cell respectively for the production of dihydrogen and the simultaneous upgrading of the overhead gases is referred to as "hydrogen pump" since it makes it possible to separate the hydrogen element from the overhead gases and to obtain it in the form of pure dihydrogen, carrying out what is referred to here as an "assisted electrolysis".

The electrolyzer performs the electrolysis reaction in which the reduction reaction from water is carried out. The presence of overhead gas at the anode 19 makes it possible to ensure that the assembly is also a fuel cell which carries out, at the anode 19, the combustion reaction described above and for which the equation of the ideal combustion reaction to give pure dioxygen (whether it is a conventional or electrochemical reaction) is presented below:

Thus, any compound of the overhead gases satisfying

$$c + \frac{h}{4} - \frac{o}{2} > 0$$

can be used in this combustion reaction, in particular:
- the carbon monoxide CO and the dihydrogen $H_2$ contained in the overhead gases recovered, corresponding to the reactants not consumed during the synthesis 10,
- the methane $CH_4$ and the heavier gaseous compounds produced by the synthesis 10 and contained in the overhead gases recovered.

The dinitrogen $N_2$ present in the overhead gases recovered may originate from the dinitrogen used as carrier gas in the gasification step 11 and from the fuel products themselves (for example 1% by weight on average for wood and coal).

It emerges finally from the aforegoing that the idea is therefore to upgrade all or some of the overhead gases resulting from the synthesis step 10 electrochemically. The electrochemical reaction carried out by a fuel cell is the most efficient combustion solution (reduced entropic losses compared to other known techniques), advantageously carried out in the presence of pure dioxygen. This thus allows a reduction of the volume of flue gases and also makes it possible to obtain carbon dioxide $CO_2$ having the lowest dilution possible, with a view to a possible collection during the collection step.

Figure 9:
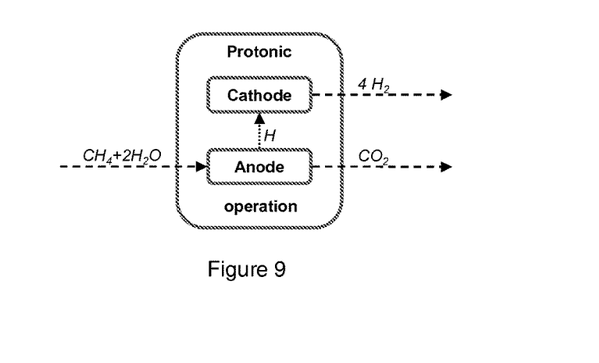

The chemical reaction formula of the hydrogen pump 14 in anionic operation, combining the reduction reaction and the combustion reaction, is the following:

In the case of protonic operation with reference to FIG. 9, the electrolysis performed in the assisted electrolysis step 18 carries out:
- an oxidation reaction on the anode 19 side, from water $H_2O$ and gases recovered in the recovering step (in particular methane $CH_4$), producing carbon dioxide $CO_2$ and hydrogen H used at the cathode 20,
- a reduction reaction on the cathode 20 side of the electrochemical device, in order to create dihydrogen $H_2$ that constitutes the dihydrogen formed in the production step of the chemical conversion process.

The main advantages of the principles of electrochemical production of dihydrogen by conversion of all or some of the overhead gases are the following:
- an improved (energy and entropic) efficiency of the recycling,
- an upgrading of the energy (contained in the material) of the overhead gases that is not limited in practice (the dihydrogen requirement is sufficiently large),
- no production of $NO_x$ in the (then electrochemical) combustion of the purge,
- the carbon dioxide is not diluted in the combustion of the purge (carried out with pure dioxygen).

Prior to the assisted electrolysis step 18, the overhead gases recovered in the recovering step may then be pressurized so that the pressure of the dihydrogen produced by the hydrogen pump 14 is equal to the pressure needed for carrying out the synthesis 10 (highly variable between atmospheric pressure and approximately 90 bar).

Furthermore, prior to the assisted electrolysis step 18, a step 17 of cracking the overhead gases resulting from the synthesis step 10 may be carried out. This cracking 17 of the overhead gases may be carried out before or after the optional pressurization described above. It may also be carried out before or after the step of recovering the overhead gases. In the case where the cracking is carried out before the recovering step, the advantage is not having to carry out an additional cracking on the fraction of the overhead gases to which the recycling step 16 is applied. In the case illustrated where the cracking 17 is carried out after the recovering step, the advantage is being able to use, for performing this cracking 17, water resulting from the step of electrochemical production of dihydrogen, at the outlet of the anode 19 and/or the cathode 20.

The chemical formula of the cracking step 17 is the following:

$$C_nH_{2 \cdot n+2} + \frac{n-1}{2} H_2O \rightarrow \frac{3 \cdot n+1}{4} \cdot CH_4 + \frac{n-1}{4} \cdot CO_2$$

The cracking step makes it possible to convert hydrocarbons having more than two carbon atoms into methane. In this case, they must first be heated at the temperature of the reaction (approximately between 400° C. and 600° C.) and this is why the vaporization step 21 is carried out, providing steam to be injected. This steam is injected in excess, the molar ratio between the water and the carbon atoms being between 2 and 5.

To carry out the vaporization step 21, water resulting from the synthesis step 10 received in the receiving step and/or at least one reused portion of water originating from the anode 19 and/or from the cathode 20 at the end of the assisted electrolysis step 18, may be used. Thus, the cracking step 17 is then applied to the gases recovered in the recovering step, with the aid of the steam formed in the vaporization step 21 from the water recovered in the receiving step and/or from the reused fraction of the total amount of water resulting from the assisted electrolysis step 18. The cracking reaction is virtually athermic and, at the outlet, the overhead gases are a mixture of dihydrogen $H_2$, water $H_2O$, methane $CH_4$, carbon monoxide CO, carbon dioxide $CO_2$ and dinitrogen $N_2$.

Advantageously, in order to optimize the general operation of the hydrogen pump 14, a heat exchange step 22 may be carried out between fluids chosen from the following list:

- overhead gases recovered during the recovering step (before and/or following the optional cracking step 17),
- water resulting (at the cathode and/or at the anode) from the assisted electrolysis step 18 and obtained after the steps of separation by condensation 25 and 26, whether it is intended for the cracking step 17 or for return to the cathode 20,
- water resulting from the synthesis and recovered during the receiving step, whether it is intended for the cracking step 17 or the cathode 20,
- output from the cathode 20 mainly containing dihydrogen,
- output from the anode 20 mainly containing carbon dioxide.

Before injection at the anode 19 of the electrochemical device that performs the assisted electrolysis 18, the overhead gases resulting from the cracking step 17 must indeed be brought to a reaction temperature between approximately 600° C. and 1100° C. depending on the electrolysis technology. This temperature rise may be achieved by recovering the heat from the gases leaving the assisted electrolysis 18 with the aid of a suitable heat exchanger that performs the heat exchange step 22. This heat recovery may also be carried out for heating the overhead gases and/or water used for the cracking step 17. The cathode 20 of the electrochemical device that performs the assisted electrolysis 18 must furthermore be supplied with steam, especially steam resulting from the vaporization step 21, previously brought to a pressure close to that of the overhead gases. Before injection at the cathode 20 of the electrochemical device that performs the assisted electrolysis 18, this steam must be brought to a reaction temperature between approximately 600° C. and 1100° C. depending on the electrolysis technology. This temperature rise may be achieved by recovering the heat from the gases leaving the assisted electrolysis with the aid of a heat exchanger that performs the heat exchange step 22.

At the anode 19, the overhead gases are oxidized, for anionic operation, to carbon dioxide $CO_2$ and water $H_2O$. The dinitrogen $N_2$ is inert. At the cathode 20, water in the form of steam originating from the heat exchanger 22 is reduced to dihydrogen $H_2$. One portion of the water is not however converted. One portion of this dihydrogen may be sent back directly or indirectly to the cathode 20 level with the heat exchanger so that the water is not pure at the inlet of the electrochemical device (indeed, up to 20% dihydrogen is needed in the incoming water at cathode 20). The streams leaving the assisted electrolysis 18 have undergone a pressure drop of less than a few bar in the heat exchangers and the electrochemical device. The assisted electrolysis is virtually athermic, possibly slightly exothermic for good operation of the heat exchanger. In the latter case, the streams leaving the electrochemical device will be 10° C. to 50° C. hotter than the incoming streams, enabling them to be used for heating the streams entering the electrochemical device. They are then cooled to a temperature between 100° C. and 300° C. approximately. They may optionally be cooled to a lower temperature, for example between 10° C. and 50° C. in order to separate the water by condensation (respectively according to the references 25 and 26 for the dihydrogen flow and for the flow of the mixture of carbon dioxide and dinitrogen). Pure dihydrogen is furthermore preferable for carrying out the synthesis step 10 in order to avoid dilution of the reactants. The separation 25, 26 of the water enables its reuse in the vaporization step 21.

Thus, the energy contained in the overhead gases is transferred directly and therefore efficiently to the dihydrogen 24 produced by the hydrogen pump 14 described above. The dihydrogen is thus separated from inert diluents (such as dinitrogen) which have a tendency to limit the feasibility of the recycling 16, and it is obtained pure (after condensation 25, 26 of water) and does not therefore have to be subjected to an additional separation. Lastly, the carbon dioxide obtained in the assisted electrolysis 18 is not diluted or is diluted very little with additional dinitrogen, making it easier to capture 23.

In addition, the chemical conversion process may advantageously comprise a step of transferring the carbon dioxide $CO_2$ recovered 23 during the collection step, to an inlet of the gasification reactor in order to form a carrier gas during the gasification step 11.

Figure 6:
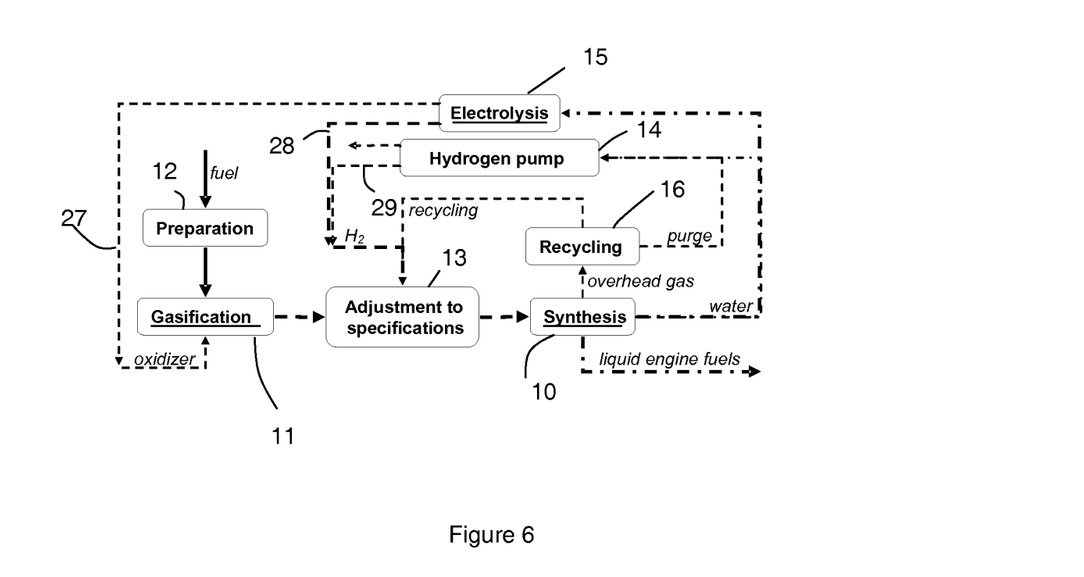
FIG. 6 represents the general principle of an example of a conversion process according to the invention.

The optional water electrolysis step 15 may advantageously use the fraction of water resulting from the synthesis step 10 and not recovered during the water receiving step, as illustrated by FIG. 6, in order to limit the overall operating cost.

Lastly, the chemical conversion process may comprise a step 28 of transferring dihydrogen $H_2$ produced during the water electrolysis step 15 to an inlet of the synthesis reactor that carries out the synthesis step 10 and/or a step 27 of transferring dioxygen produced during the water electrolysis step 15 to an inlet of the gasification reactor that carries out the gasification step 11 to form an oxidizing compound during the gasification step 11.

The invention also relates to the chemical conversion plant as such, especially for conversion of fuels such as coal, oil, biomass or natural gas, into at least one synthetic compound, especially a liquid engine fuel such as an alkane and/or an alkene, this plant comprising for this purpose the equipment and/or software components that carry out the conversion process described above. It lastly relates to the computer program comprising a computer program code means suitable for the implementation of the steps of the conversion process when the program is executed by a computer of the plant.

Simulations have been carried out, for example using process simulation software sold under the name ProSim-Plus®, starting from the following hypotheses:
  use of biomass as the fuel product at the inlet of the conversion,
  use of carbon dioxide (case 1) and of dinitrogen (case 2) as carrier gas during the gasification step 11,
  the implementation of a "Fischer-Tropsch" type synthesis step for the production of liquid engine fuels.

The results described in detail further on are presented solely as regards the water electrolysis step 15 of high-temperature steam electrolysis (known under the acronym "HTSE") type and the assisted electrolysis 18 carried out by the hydrogen pump 14. More specifically, for each of case 1 (use of carbon dioxide as carrier gas) and case 2 (use of dinitrogen as carrier gas), the results show the comparison between the simulated situations corresponding respectively, on the one hand, to the case where only the water electrolysis step 15 would be applied and, on the other hand, to the case where this water electrolysis step 15 would be carried out at the same time as a step of electrochemical production of dihydrogen by the hydrogen pump 14.

In case 1 where the carbon dioxide is used as carrier gas, the simulations show that the overhead gases resulting from the synthesis step have the following composition:

|  | kg/s | mol/s | wt % | mol % |
|---|---|---|---|---|
| $H_2$ | 0.30 | 151 | 3% | 33% |
| $N_2$ | 2.37 | 84 | 27% | 19% |
| CO | 2.35 | 84 | 26% | 18% |
| $CH_4$ | 1.24 | 78 | 14% | 17% |
| $C_2H_6$ | 0.17 | 6 | 2% | 1% |
| $CO_2$ | 1.65 | 37 | 19% | 8% |
| $C_3H_8$ | 0.27 | 6 | 3% | 1% |
| $C_4H_{10}$ | 0.36 | 6 | 4% | 1% |
| $C_5H_{12}$ | 0.09 | 1 | 1% | 0% |
| $C_6H_{14}$ | 0.03 | 0 | 0% | 0% |
| $C_7H_{16}$ | 0.01 | 0 | 0% | 0% |
| $H_2O$ | 0.03 | 2 | 0% | 0% |

Next, following a step of adding 3.32 kg/s (184 mol/s) of water and a step 17 of cracking chains having more than two carbon atoms, the simulations show that the overhead gases have the following composition:

|  | kg/s | mol/s | wt % | mol % |
|---|---|---|---|---|
| $H_2$ | 0.30 | 151 | 2% | 23% |
| $N_2$ | 2.37 | 84 | 19% | 13% |
| CO | 2.35 | 84 | 19% | 13% |
| $CH_4$ | 2.10 | 131 | 17% | 20% |
| $CO_2$ | 2.14 | 49 | 18% | 7% |
| $H_2O$ | 2.94 | 163 | 24% | 25% |

By taking a hypothesis according to which only 20% of these overhead gases are purged (and are therefore sent to the hydrogen pump 14 and used for the assisted electrolysis step 18), the remaining 80% of the overhead gases undergo a conventional recycling step 16. The hydrogen pump 14 then provides 0.31 kg/s (153 mol/s) of dihydrogen to the cathode 20. The stream leaving the anode 19 is itself constituted in the following manner:

|  | kg/s | mol/s | wt % | mol % |
|---|---|---|---|---|
| $N_2$ | 0.47 | 17 | 10% | 9% |
| $CO_2$ | 2.32 | 53 | 48% | 28% |
| $H_2O$ | 2.08 | 115 | 43% | 62% |

After a condensation 26 of the water over the stream leaving the anode 19, the carbon dioxide represents 83% by weight and 75% by material of the outgoing flow. This high value enables a facilitated capture. The reuse of water makes it possible to limit the consumption thereof by the hydrogen pump 14 to 1.34 kg/s (75 mol/s), i.e. 49 mol % of the production of dihydrogen by the heat pump. The electricity consumption of the assisted electrolysis 18 is 3.27 MW, i.e. 10.5 MJ per kilogram of dihydrogen produced electrochemically. The total production of dihydrogen, combining that obtained by the step 18 of electrolysis assisted by the overhead gases, is 2.25 kg/s (1115 mol/s), for 244 MW needed for the reactions, i.e. 108 MJ per kilogram of dihydrogen on average. In comparison, the simple electrolysis 15 of water requires 124 MJ per kilogram of dihydrogen obtained.

Overall, regarding the process for the chemical conversion of biomass, the solution proposed here of assisted electrolysis 18 makes it possible to reduce the electricity consumption by 12%. This performance is partly counter-balanced by a greater requirement for high-temperature heat, provided by natural gas. The savings in secondary energies (corresponding to the energies consumed by the process and measured at the input of the process) then become of the order of 1.5%. The configuration studied is particularly unfavourable to assisted electrolysis 18 since simple electrolysis 15 makes it possible to provide exactly the amount of dioxygen needed for the gasification 11 (the assisted electrolysis 18 then creates an electricity requirement for the production of dioxygen) and the heat provided by the purge is of the same order as the requirement for the reforming of the recycling step 16 (the assisted electrolysis 18 then creates a natural gas requirement in order to provide heat to this reaction). The efficiencies are obtained by dividing the energy contained in the engine fuels at the output of the process by the energy consumed at the input of the process:

| (powers in MW) | Hydrogen pump and HTSE | HTSE alone |
|---|---|---|
| Wet biomass | 477 | 477 |
| Electricity | 246 | 278 |
| Heat (natural gas) | 21 | 0 |
| Total secondary energy | 744 | 755 |
| Total primary energy (electricity*3) | 1 236 | 1 312 |
| Engine fuels | 462 | 462 |
| Losses | 282 | 293 |
| Secondary energy efficiency | 62% | 61% |
| Primary energy efficiency | 37% | 35% |

Now, in case 2 where the dinitrogen is used as carrier gas, the simulations show that the overhead gases resulting from the synthesis step have the following composition:

| | kg/s | mol/s | wt % | mol % |
|---|---|---|---|---|
| $H_2$ | 0.21 | 103 | 1% | 17% |
| $N_2$ | 10.99 | 392 | 73% | 64% |
| CO | 1.60 | 57 | 11% | 9% |
| $CH_4$ | 0.36 | 22 | 2% | 4% |
| $C_2H_6$ | 0.12 | 4 | 1% | 1% |
| $CO_2$ | 1.09 | 25 | 7% | 4% |
| $C_3H_8$ | 0.19 | 4 | 1% | 1% |
| $C_4H_{10}$ | 0.25 | 4 | 2% | 1% |
| $C_5H_{12}$ | 0.09 | 1 | 1% | 0% |
| $C_6H_{14}$ | 0.04 | 0 | 0% | 0% |
| $C_7H_{16}$ | 0.01 | 0 | 0% | 0% |
| $H_2O$ | 0.03 | 2 | 0% | 0% |

Next, following a step of adding 2.37 kg/s (131 mol/s) of water and a step 17 of cracking chains having more than two carbon atoms, the simulations show that the overhead gases have the following composition:

| | kg/s | mol/s | v | mol % |
|---|---|---|---|---|
| $H_2$ | 0.21 | 103 | 1% | 14% |
| $N_2$ | 10.99 | 392 | 63% | 51% |
| CO | 1.60 | 57 | 9% | 7% |
| $CH_4$ | 0.99 | 62 | 6% | 8% |
| $CO_2$ | 1.46 | 33 | 8% | 4% |
| $H_2O$ | 2.09 | 116 | 12% | 15% |

By taking a hypothesis according to which only all of these overhead gases are purged (and are therefore sent to the hydrogen pump 14 and used for the assisted electrolysis step 18), the conventional recycling step 16 is not carried out. The hydrogen pump 14 then provides 0.84 kg/s (415 mol/s) of dihydrogen to the cathode 20. The stream leaving the anode 19 is itself constituted in the following manner:

| | kg/s | mol/s | wt % | mol % |
|---|---|---|---|---|
| $N_2$ | 10.98 | 392 | 46% | 44% |
| $CO_2$ | 6.69 | 152 | 28% | 17% |
| $H_2O$ | 6.17 | 342 | 26% | 38% |

The cooling of all of the dihydrogen produced, on the one hand, by simple electrolysis 15 of water and, on the other hand, by electrolysis 18 assisted by the overhead gases, by the hydrogen pump 14 makes it possible to heat the overhead gases resulting from the cracking step 17 from 535° C. to 770° C., to vaporize 21 the water for the cracking step 17 and to bring it to 500° C. The dihydrogen is thus cooled to 160° C. The cooling of the output from the anode 19 makes it possible to superheat the steam from 240° C. to 770° C. and heat the liquid water for the electrolyses 15 and 18 up to 210° C.

After a condensation 26 of the water, the carbon dioxide represents 38% by weight and 28% by material of the flow leaving the anode 19. This value is much lower than above for case 1, given the amounts of dinitrogen injected. The reuse of water makes it possible to limit the consumption thereof by the hydrogen pump 14 to 1.81 kg/s (101 mol/s), i.e. 24 mol % of the production of dihydrogen by the hydrogen pump. The electricity consumption of the assisted electrolysis 18 is 7.14 MW, i.e. 8.5 MJ per kilogram of dihydrogen produced electrochemically by conversion of the overhead gases. The total production of dihydrogen, combining that obtained by the water electrolysis step 15 and that obtained by the step 18 of electrolysis assisted by the overhead gases, is 1.29 kg/s (638 mol/s), for 63 MW needed for the reactions, i.e. 49 MJ per kilogram of dihydrogen. In comparison, the simple electrolysis 15 of water requires 124 MJ per kilogram of dihydrogen obtained.

Overall, regarding the process for the chemical conversion of biomass, the solution proposed here of assisted electrolysis 18 makes it possible to reduce the electricity consumption by 32%, despite a greater requirement for dioxygen, obtained by air separation. The savings in secondary energies are 6.7%. The configuration studied is particularly favourable to assisted electrolysis 18 since the amount of inert compound injected into the process is such that all the overhead gases resulting from the synthesis 10 must be purged (the upgrading of these overhead gases electrochemically by the hydrogen pump 14 is more effective than upgrading via combustion followed by production of electricity). The efficiencies are obtained by dividing the energy contained in the engine fuels at the output of the process by the energy consumed at the input of the process:

| (powers in MW) | Hydrogen pump and HTSE | HTSE alone |
|---|---|---|
| Wet biomass | 477 | 477 |
| Electricity | 87 | 127 |
| Heat (natural gas) | 0 | 0 |
| Total secondary energy | 564 | 605 |
| Total primary energy (electricity*3) | 738 | 860 |
| Engine fuels | 315 | 315 |
| Losses | 250 | 290 |
| Secondary energy efficiency | 56% | 52% |
| Primary energy efficiency | 43% | 37% |

Finally, the preceding simulations show that overall for the process for the chemical conversion of biomass, it may be estimated that by using a "Fischer-Tropsch" synthesis for the production of liquid engine fuels, the solution proposed here of electrolysis 18 assisted by the overhead gases makes it possible to reduce the secondary energy consumption of the process by 0 to 10%. The advantages already alluded to and illustrated by the simulations are mainly:
good (energy and entropic) efficiency of the recycling 16,
an upgrading of the energy (contained in the material) of the overhead gases that is not limited in practice,
an absence of the production of $NO_x$ during the (then electrochemical) combustion of the purge,
the carbon dioxide produced is not diluted during the combustion of the purge (carried out in the presence of pure dioxygen).

The advantage as regards the non-dilution of the carbon dioxide is quantified in concentrations but is not quantified energetically, the capture of this compound not being carried out in the above simulations.

The invention claimed is:

1. Chemical conversion process comprising:
    a synthesis step that takes, as input, reactants that include at least dihydrogen and carbon monoxide and that gives, as output, a synthetic compound, water and overhead gases,
    a step of recovering all or some of the overhead gases resulting from the synthesis step, and
    a step of electrochemically producing dihydrogen by an assisted electrolysis which comprises electricity consumption, the assisted electrolysis including a conversion of $C_cH_hO_o$ compounds satisfying $C+h/4-o/2>0$ contained in the overhead gases recovered in the recovering step, electrochemically and in a manner that creates said dihydrogen.

2. Conversion process according to claim 1, comprising a step of transferring the dihydrogen formed in the dihydrogen producing step to an inlet of a synthesis reactor that carries out the synthesis step.

3. Conversion process according to claim 2, comprising a step of cracking the overhead gases resulting from the synthesis step.

4. Conversion process according to claim 2, wherein the assisted electrolysis is on the anode side of an electrochemical device, by the overhead gases recovered in the recovering step.

5. Conversion process according to claim 1, comprising a step of cracking the overhead gases resulting from the synthesis step.

6. Conversion process according to claim 1, wherein the assisted electrolysis is on the anode side of an electrochemical device, by the overhead gases recovered in the recovering step.

7. Conversion process according to claim 6, comprising a step of receiving all or some of the water resulting from the synthesis step, the assisted electrolysis step using water recovered in the receiving step.

8. Conversion process according to claim 7, wherein fuel products are converted so as to form, at the end of the synthesis step, at least one synthetic compound consisting of a liquid engine fuel, and wherein the process comprises a step of electrolysis of water, using the fraction of water resulting from the synthesis step and not recovered during the water receiving step.

9. Conversion process according to claim 8, comprising a step of transferring dihydrogen produced during the water electrolysis step to an inlet of the synthesis reactor that carries out the synthesis step and/or a step of transferring dioxygen produced during the water electrolysis step to an inlet of the gasification reactor that carries out the gasification step to form an oxidizing compound during the gasification step.

10. Conversion process according to claim 6, wherein the electrolysis carried out in the assisted electrolysis is of anionic type and carries out:
    a reduction reaction from water, on the cathode side of the electrochemical device, producing on the one hand some dihydrogen that constitutes the dihydrogen formed in the dihydrogen producing step, and on the other hand oxygen,
    a combustion reaction on the anode side, between the oxygen resulting from the reduction reaction and the overhead gases recovered in the recovering step, in order to produce water and carbon dioxide.

11. Conversion process according to claim 10, wherein the cracking step is applied to the gases recovered in the recovering step using steam formed from the water recovered in the receiving step and/or a reused fraction of the total amount of water resulting from the assisted electrolysis.

12. Conversion process according to claim 10, comprising a step of collecting carbon dioxide produced during the combustion reaction at the anode.

13. Conversion process according to claim 6, wherein the electrolysis carried out in the assisted electrolysis is of protonic type and carries out:
    an oxidation reaction on the anode side, from water and gases recovered during the recovering step, producing carbon dioxide,
    a reduction reaction on the cathode side of the electrochemical device, in order to create some dihydrogen that constitutes the dihydrogen formed in the dihydrogen producing step.

14. Conversion process according to claim 1, comprising a step of heat exchange between fluids selected from the following list: overhead gases recovered during the recovering step, dihydrogen and/or water and/or carbon dioxide and/or dinitrogen resulting from the assisted electrolysis, gases resulting from the cracking step, water recovered during the receiving step and carbon dioxide recovered during the collection step.

15. Conversion process according to claim 1, in which fuel products are converted so as to form, at the end of the synthesis step, at least one synthetic compound consisting of a liquid engine fuel.

16. Conversion process according to claim 15, comprising a gasification step, in a gasification reactor, that takes, as input, at least said fuel products and that gives, as output, reactants that include at least one portion of the dihydrogen and of the carbon monoxide used during the synthesis step.

17. Conversion process according to claim 16, comprising a step of transferring the carbon dioxide recovered during the carbon dioxide collection step to an inlet of the gasification reactor in order to form a carrier gas during the gasification step.

18. Conversion process according to claim 15, comprising a step of recycling the fraction of overhead gas resulting from the synthesis step and not recovered during the overhead gas recovering step.

19. Non-transitory computer readable medium carrying a computer program comprising a computer program code suitable for the implementation of the steps of a process, when the program is executed by a computer,
    wherein the implemented process is a conversion process comprising:

a synthesis step that takes, as input, reactants that include at least dihydrogen and carbon monoxide and that gives, as output, a synthetic compound, water and overhead gases, a step of recovering all or some of the overhead gases resulting from the synthesis step, and a step of electrochemically producing dihydrogen by an assisted electrolysis which comprises electricity consumption, the assisted electrolysis including a conversion of $C_cH_hO_o$ compounds satisfying $C+h/4-o/2>0$ contained in the overhead gases recovered in the recovering step, electrochemically and in a manner that creates said dihydrogen.

20. Chemical conversion plant comprising the computer readable medium according to claim 19, a computer, and chemical conversion equipment, wherein the chemical conversion equipment is configured to implement the conversion process when the program carried by the computer readable medium is executed by the computer.

* * * * *